US008878432B2

(12) United States Patent
Chen et al.

(10) Patent No.: US 8,878,432 B2
(45) Date of Patent: Nov. 4, 2014

(54) ON BOARD DIAGNOSIS OF RF SPECTRA IN ACCELERATORS

(75) Inventors: Gongyin Chen, Henderson, NV (US); John C. Turner, Las Vegas, NV (US)

(73) Assignee: Varian Medical Systems, Inc., Palo Alto, CA (US)

( * ) Notice: Subject to any disclaimer, the term of this patent is extended or adjusted under 35 U.S.C. 154(b) by 66 days.

(21) Appl. No.: 13/589,920

(22) Filed: Aug. 20, 2012

(65) Prior Publication Data

US 2014/0049158 A1 Feb. 20, 2014

(51) Int. Cl.
| | |
|---|---|
| *H01J 25/10* | (2006.01) |
| *A61N 5/10* | (2006.01) |
| *H01J 29/98* | (2006.01) |
| *H05H 9/00* | (2006.01) |
| *H05H 7/02* | (2006.01) |

(52) U.S. Cl.
CPC .............. *H01J 29/98* (2013.01); *A61N 5/1048* (2013.01); *H05H 2007/025* (2013.01); *H05H 9/00* (2013.01); *H05H 7/02* (2013.01)
USPC ........... 315/5.41; 315/500; 315/502; 315/505

(58) Field of Classification Search
USPC ........................................ 315/5.41, 500–505
See application file for complete search history.

(56) References Cited

U.S. PATENT DOCUMENTS

| | | | |
|---|---|---|---|
| 5,044,006 A | | 8/1991 | Cyrulnik |
| 5,497,050 A | * | 3/1996 | Cheo ............................ 315/5.41 |
| 6,140,752 A | * | 10/2000 | Seward et al. ............ 313/231.31 |
| 6,744,226 B2 | * | 6/2004 | Yu et al. ......................... 315/505 |
| 7,619,374 B2 | * | 11/2009 | Aoi et al. ....................... 315/500 |
| 7,626,347 B2 | * | 12/2009 | Sliski et al. .................... 315/502 |
| 8,067,748 B2 | * | 11/2011 | Balakin .................. 250/396 ML |
| 8,159,158 B2 | * | 4/2012 | Popovic et al. ............... 315/500 |
| 8,183,801 B2 | * | 5/2012 | Chen et al. .................... 315/505 |
| 8,373,146 B2 | * | 2/2013 | Balakin ...................... 250/492.3 |
| 8,624,528 B2 | * | 1/2014 | Balakin ......................... 315/503 |
| 2008/0128641 A1 | * | 6/2008 | Henley et al. ............ 250/492.21 |
| 2010/0038563 A1 | | 2/2010 | Chen et al. |
| 2012/0280685 A1 | * | 11/2012 | Hadley et al. ................. 324/309 |
| 2012/0281957 A1 | * | 11/2012 | Chamanzar et al. .......... 385/131 |

OTHER PUBLICATIONS

International Search Report and Written Opinion dated Jan. 17, 2014 for PCT Patent Application No. PCT/US2013/055616, 10 pages.

\* cited by examiner

*Primary Examiner* — Douglas W Owens
*Assistant Examiner* — Srinivas Sathiraju
(74) *Attorney, Agent, or Firm* — Vista IP Law Group, LLP (57) ABSTRACT

A RF accelerator system includes an accelerator, a RF source coupled to the accelerator for providing RF power to the accelerator, a control for adjusting a frequency of the RF power provided by the RF source through a frequency range, and a sensor for sensing a response resulted from an operation of the accelerator based at least in part on the adjusted frequency of the RF power through the frequency range. A method of diagnosing a RF spectrum in an accelerator system includes providing RF power to an accelerator, adjusting a frequency of the RF power through a frequency range, and sensing a response resulted from an operation of the accelerator, the response being based at least in part on the adjusted frequency of the RF power through the frequency range.

30 Claims, 9 Drawing Sheets

An example of good or
normal response

FIG. 5A

An example of bad response indicating
possible RF source malfunction

Measurement result from swapping RF source
frequency–using reflected RF from a SW accelerator.

An example of good or normal response

FIG. 7A

An example of bad response indicating
possible RF source malfunction

Measurement result from swapping RF source
frequency–using passing-through RF of extra cavity.

ON BOARD DIAGNOSIS OF RF SPECTRA IN ACCELERATORS

FIELD

This application relates generally to systems that include particle accelerators, and more specifically, to devices for diagnosing component(s) in such accelerator systems.

BACKGROUND

RF electron beam accelerators have found wide usage in medical accelerators where the accelerated high energy electron beam is employed to generate x-rays for therapeutic and diagnostic purposes. Electron beams generated by an electron beam accelerator can also be used directly or indirectly to kill infectious agents and pests, to sterilize objects, to change physical properties of objects, and to perform testing and inspection of objects, such as containers, containers storing radioactive material, and concrete structures.

In radiofrequency (RF) accelerators, particle acceleration may be powered by feeding RF power into the accelerator cavities. The accelerating cavities may have a loaded Q value of a few thousands to more than ten thousands. The resonance frequency of acceleration may drift with heating, and the RF source frequency may be "tuned" (e.g., adjusted with a servo) to match frequency of the cavities. When the accelerator is operated with a magnetron, the tuning action may be accomplished by adjusting the frequency tuner. When the accelerator is operated with a klystron, the tuning action may be accomplished by adjusting the frequency control voltage of the voltage controlled oscillator (VCO) in the RF driver.

In either case, the RF source is assumed to work properly. The desired RF spectrum has most power at cavity frequency, with small amplitude side lobes. When the RF source produces RF power but its spectrum becomes bad (e.g., main lobe has lower amplitude and wide peak width), existing RF power monitors may not be able to identify the problem. While the RF source may still produce RF power output, the spectral quality of the output will have a deteriorated quality. In some cases, a sophisticated spectrum analyzer may be used for off-line diagnosis of such problem. Such off-line spectrum analyzer is configured to measure the RF spectra from the RF source. It is expensive and complicated to use, and may not be readily available in some cases.

SUMMARY

In accordance with some embodiments, an RF accelerator system includes an accelerator, an RF source coupled to the accelerator for providing RF power to the accelerator, a control for adjusting a frequency of the RF power provided by the RF source through a frequency range, and a sensor for sensing a response resulted from an operation of the accelerator based at least in part on the adjusted frequency of the RF power through the frequency range.

In accordance with other embodiments, a method of diagnosing RF spectrum in an accelerator system includes providing RF power to an accelerator, adjusting a frequency of the RF power through a frequency range, and sensing a response resulted from an operation of the accelerator, the response being based at least in part on the adjusted frequency of the RF power through the frequency range.

Other and further aspects and features will be evident from reading the following detailed description of the embodiments.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings are not to be considered limiting in the scope of the claims.

DESCRIPTION OF THE EMBODIMENTS

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the claimed invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

Figure 1:
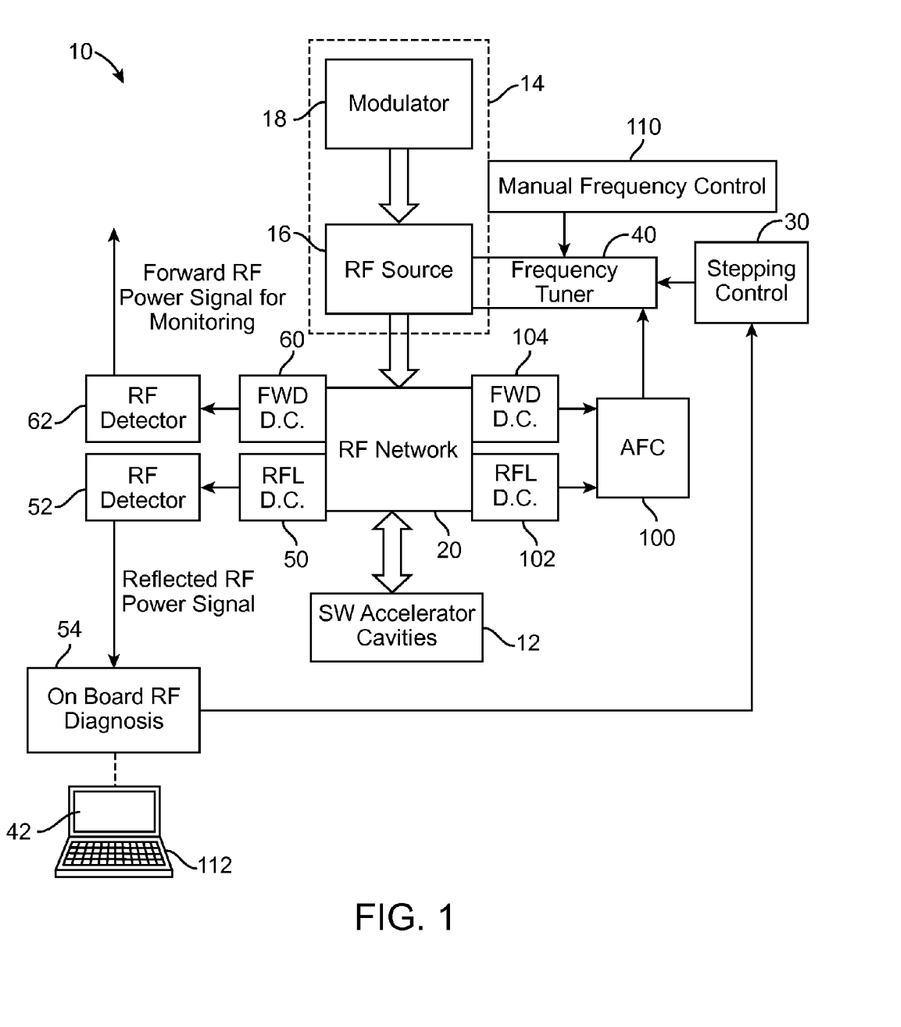
FIG. 1 is a block diagram of an accelerator system in accordance with some embodiments.

FIG. 1 is a block diagram of a standing wave accelerator system 10 in accordance with some embodiments. The accelerator system 10 includes a particle accelerator 12 coupled to an RF power system 14, which includes an RF power generator 16 and an electric power modulator system 18. The accelerator 12 may be a part of a medical treatment device, such as a radiation machine for delivering treatment radiation beam, or a diagnostic device, such as an imaging machine (e.g., an X-ray machine, a CT machine, etc.). In other embodiments, the accelerator 12 may be a part of an inspection system, such as an object inspection system. The accelerator 12 may include a plurality of axially aligned cavities (electromagnetically coupled resonant cavities). The accelerator system 10 may also include a particle source (e.g., an electron gun) for injecting particles such as electrons into the accelerator 12.

During use, the accelerator 12 is excited by power, e.g., microwave power, delivered by the RF power system 14 at a frequency, for example, at least between 0.5 GHz and 35 GHz, or at other frequencies. The RF power generator 16 may be a magnetron, a klystron, both of which are known in the art, or any of other power generating devices that is capable of providing RF power. In some embodiments, the RF power generator 16 may be a solid state RF oscillator plus a klystron amplifier. The power delivered by the RF power system 14 is in the form of electromagnetic waves. The electrons generated by the particle source are accelerated through the accelerator 12 by oscillations of the electromagnetic waves within the cavities of the accelerator 12, thereby resulting in an accelerated electron beam.

The electric power modulator 18 is configured (e.g., built and/or tuned) to adjust an amplitude of the output power of the RF power source 16. For example, in some embodiments, the electric power modulator 18 comprises a pulse modulator that drives the RF power source 16, in which case, the electric power modulator 18 is configured to adjust the amplitude of the pulse from the pulse modulator in order to decrease or increase the output power from the RF power source 16. In the illustrated embodiments, the electric power modulator 18 is illustrated as a separate component from the RF power source 16. In other embodiments, the electric power modulator 18 and the power source 16 may be integrated together.

In the illustrated embodiments, the RF source 16 is coupled to the accelerator 12 through a RF network 20. The RF network 20 may include one or more RF components that are configured to transmit RF power from the RF power source 16 to the accelerator 12, and to prevent most of reflected RF power from the accelerator 12 from being transmitted back to the RF power source 16. By means of non-limiting examples, the RF network 20 may include RF isolators, RF circulators, RF loads, and accessories. Also, in some embodiments, the RF network 20 may include different waveguides coupled to different parts (e.g., cavities) of the accelerator 12.

Figure 2A:
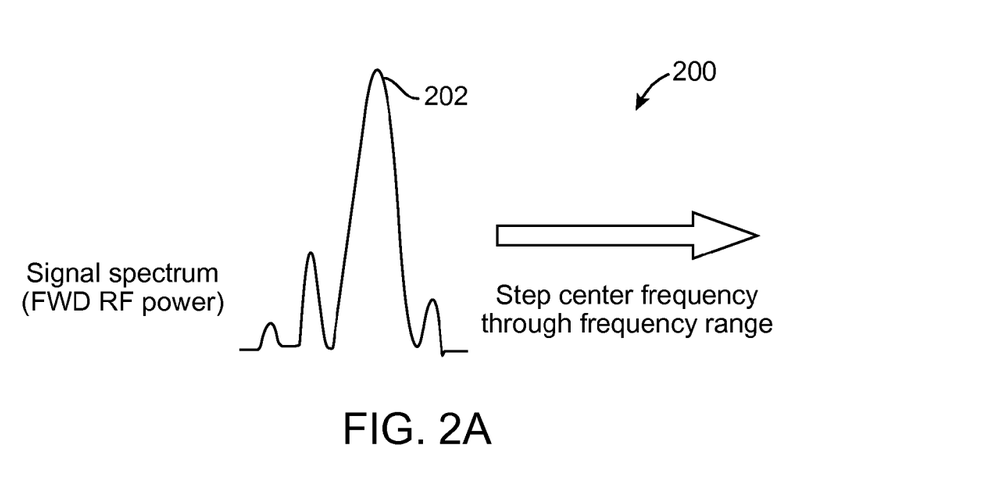
FIG. 2A illustrates an example of a signal spectrum associated with a forward RF power.

As shown in FIG. 1, the accelerator system 10 also includes a frequency tuner 40 coupled to the RF power source 16. The frequency tuner 40, in turn, may be controlled by an AFC 100 (automatic frequency control), a manual frequency control 110, or a stepping control 30. During normal machine operation, The AFC 100 controls the frequency tuner 40 so that center frequency of the RF source 16 is adjusted to match the resonance frequency of the accelerator 12. The manual frequency control allows an operator or service person to adjust the center frequency of the RF source 16 to match or mismatch the resonance frequency of the accelerator 12 during machine setup process. In accordance with some embodiments, the step control 30 is configured to adjust a center frequency of the RF source 16 in small steps to accommodate on board RF spectrum diagnosis. The step control 30 is configured to generate signals for controlling an operation of the frequency tuner 40, and the frequency tuner 40 is configured to control the power source 16 so that the forward power from the power source 16 has a signal spectrum with a certain center frequency. In the illustrated embodiments, the step control 30 is configured to generate signals (e.g., in response to a control signal from processor 54) to control the frequency tuner 40 so that the forward power from the power source 16 has a center frequency that is stepped through a number of prescribed values. The prescribed values may be in an increasing order, in a decreasing order, or in a customized order. FIG. 2A illustrates an example of the forward power (source) spectrum 200 with a peak 202, wherein the center frequency of the spectrum 200 may be stepped over a predetermined range. During RF spectrum diagnosis, the frequency tuner 40 operates the power source 16 in response to signals provided by the step control 30 so that the peak 202 of the power spectrum 200 is sequentially adjusted to different pre-determined values. For example with an X-band accelerator, the center frequency may be near 9,300,000 GHz. It may be scanned in a 2,000 kHz range in 50 kHz steps. The filter response valley 201 (accelerator 12 reflection vs. frequency) is inside the frequency scanning range. It should be noted that although the peak 202 location is called "center frequency", it may not necessarily be at the exact center of the spectrum 200, and the spectrum 200 may not be exactly symmetric with an exact "center" at all. Thus, the term "center frequency" refers to the frequency where the peak 202 is located, and it may or may not necessarily be at the exact center of the spectrum 200. In the illustrated embodiments, the step control 30 is a separate component from the frequency tuner 40 and the processor 54. In other embodiments, the step control 30 may be implanted as a part of the processor 54. Also, in some embodiments, the step control 30 may be implemented using a processor.

Figure 2B:
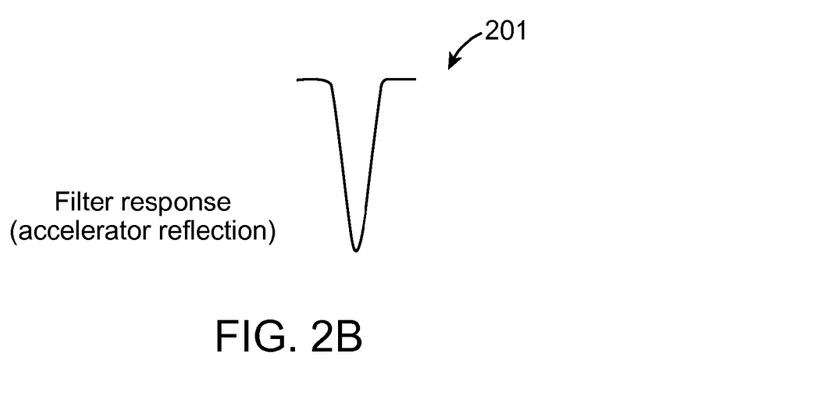
FIG. 2B illustrates an example of a filter frequency response of an accelerator in accordance with some embodiments.

In the illustrated embodiments, the accelerator system 10 also includes a reflected RF directional coupler 50, a sensor 52 coupled to the processor 54. The accelerator 12 may be considered a resonant load and signal (power) reflected therefore may vary with input spectrum frequency. During on board diagnosis, which may take a few seconds or less, the filter response of the accelerator 12 (e.g., accelerator 12's reflection vs. frequency) may be considered not changing. FIG. 2B illustrates an example of a filter frequency response 201 of the accelerator 12 in accordance with some embodiments. The directional coupler 50 is configured to direct RF power that is reflected back from the accelerator 12 towards the RF power source to the sensor 52. The sensor 52 is configured to generate a signal (electrical signal) in response to the detected reflected RF power transmitted from the coupler 50. In the illustrated embodiments, the directional coupler 50 is coupled to the accelerator 12 through the RF network 20, which may include a network of RF components configured to transmit RF signals from the accelerator 12 to the directional coupler 50. In some embodiments, the RF network 20 may include a circulator/isolator inserted anywhere along the RF network 20 between the RF source 16 and the accelerator 12. In such cases, the directional coupler 50 may be at a location where reflected RF power is present. The directional coupler 50 may be implemented using any form of a transmission line, as long as the directional coupler 50 can sample power reflected back from the accelerator 12.

In the illustrated embodiments, the sensor 52 is electrically coupled to the processor 54, and is configured to provide a voltage for the processor 54 that corresponds with a level of RF power sensed by the directional coupler 50. In some embodiments, the sensor 52 functions as an adaptor that interfaces between the directional coupler 50 and the processor 54. In any of the embodiments described herein, instead of being a component that is separate from the processor 54 and the directional coupler 50, the sensor 52 may be a part of the processor 54, or alternatively, a part of the directional coupler 50. It should be noted that the sensor 52 may be implemented using any device as long as it can convert sensed RF power to current. Devices that are capable of converting a RF signal to current is well known, and may be used to implement the sensor 52. For example, in some embodiments, the sensor 52 may be a diode detector, or another type of detector. Also, in some embodiments, the detector may include an input port for receiving RF power, and an output for providing a voltage.

In some embodiments, any or a combination of the sensor 52, the processor 54, the step control 30, and the frequency tuner 40 may be a part of the power system 14.

During RF spectrum diagnosis, the frequency tuner 40 operates the RF power source 16 to generate RF power across a frequency range, one center frequency at a time across a desired frequency range that include the frequency filter response 201. At the same time, the reflected RF power from the accelerator 12 is sampled by the directional coupler 50 and is transmitted to the sensor 52. The sensor 52 generates signals in response to the reflected power while the center frequency of the forward power spectrum is adjusted to different pre-determined values, and transmits the signals to the processor 54 for processing. The processor 54 sends frequency stepping command to stepping control 30, one data point at a time, which in turn controls frequency tuner 40 to change center frequency of RF source 16, one data point at a time. When RF power is generated at each center frequency point, the processor 54 records the reflected RF signal from sensor 52. The resulting data pairs (center frequency vs. reflected RF power) form a spectrum (which may be recorded), and the spectrum may be used to determine whether the RF source 16 is working properly. In some embodiments, the signals from the sensor 52 may be displayed in a screen 42 in a form of a spectrum.

Figure 3:
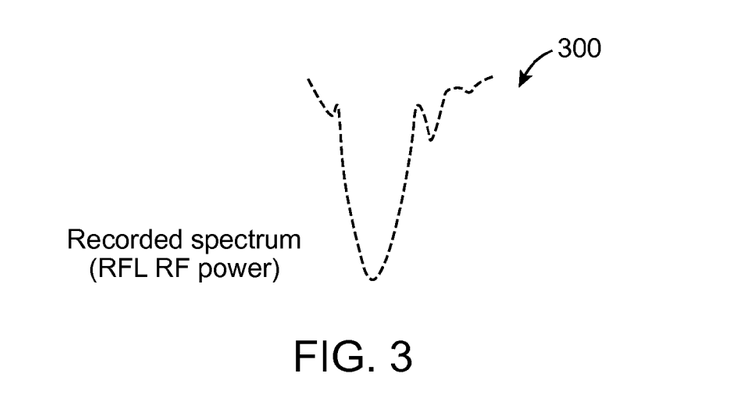
FIG. 3 illustrates an example of a signal spectrum obtained during a diagnostic procedure.

FIG. 3 illustrates an example of a spectrum 300 generated using the sensor 52 when the accelerator system 10 (e.g., the power source 16 of the accelerator system 10) is working properly. In some embodiments, the spectrum 300 may be considered as a convolution of the RF source spectrum 200 and the filter response 201. As shown in FIGS. 2-3, the filter response 201 is the reflection rate at various frequencies, and may be treated as not changing during the diagnosis process, which takes no more than a few seconds in some embodiments. At each center frequency, the portion of source spectrum 200 that does not overlap the filter response 201 is reflected and sampled by directional coupler. The sampled signal is detected and recorded as one data point in a recorded spectrum 300—i.e., each recorded data point is a (center frequency, total reflected power) pair. The portion of the RF spectrum 200 that overlaps and aligns with the filter response 201 has minimal reflection, and the portion of RF spectrum 200 that aligns on the shoulder of filter response 201 is fully reflected, thereby resulting in the recorded spectrum 300.

Figure 5A:
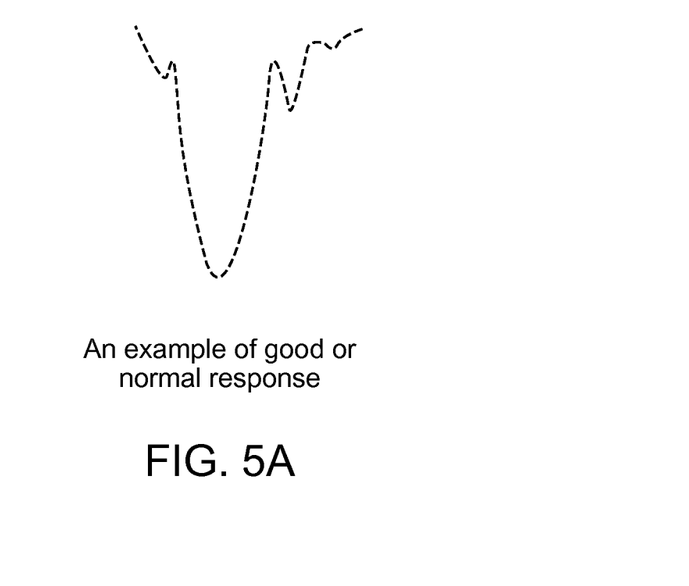
FIGS. 5A-5B illustrate examples of response spectrums in accordance with some embodiments.
Figure 5B:
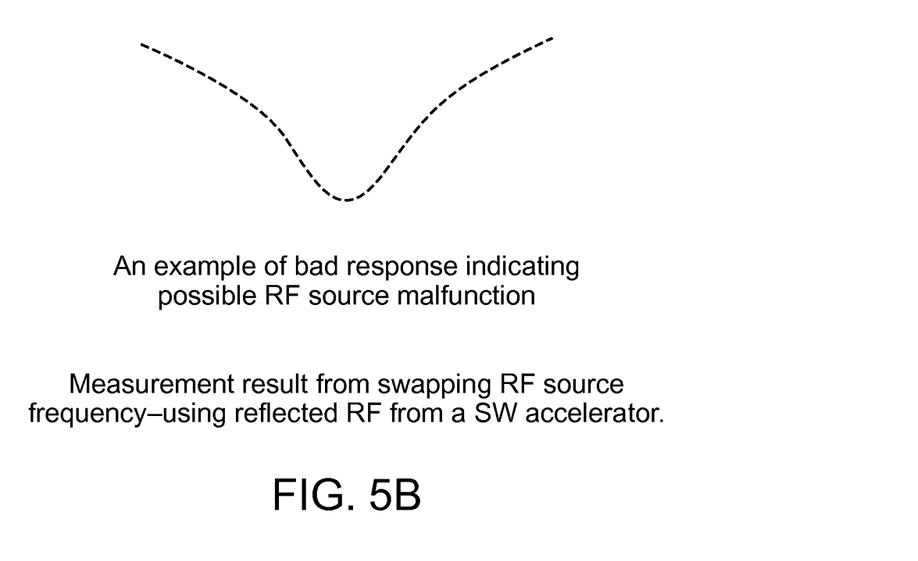

Also, in some embodiments, the spectrum 300 may be stored in a non-transitory medium for further processing. Such spectrum 300, which is generated when the RF source 16 is working properly, may be used as a reference spectrum for comparison with later generated spectrums. For example, in some embodiments, the stored spectrum 300 resulted from a previous diagnostic procedure may be compared as a reference spectrum with another spectrum generated from a later diagnostic procedure, and the comparison result may be used to determine whether the accelerator system 10 is performing properly. For example, if the new spectrum (like that shown in FIG. 5A) generated from the current or recent diagnostic procedure looks like the stored spectrum (generated when the accelerator system 10 is working properly) like that shown in FIG. 3, then it may be determined that the accelerator system 10 is still working properly. On the other hand, if the new spectrum (like that shown in FIG. 5B) looks different from the stored spectrum, it may then be determined that the accelerator system 10 is not working properly. In some embodiments, the processor 54 may be a comparator configured (e.g., built and/or programmed) to compare the output from the sensor 52 with a previously stored response. The comparator 54 may be implemented using a processor, a computer, or any other circuit. It should be noted that the term "compare" (and similar terms, such as "comparing"), as used in this specification, is not limited to the act of determining a difference using two items, and may refer to the act of performing any operation using two or more items. Similarly, the term "comparator" as used in this specification is not limited to a device that determines a difference using two items, and may be a device that performs any operation using two or more items.

As shown in the figure, the accelerator system 10 may optionally further include a forward RF directional coupler 60 coupled to the RF network 20, and a sensor 62 coupled to the directional coupler 60. The sensor 62 may be a RF detector in some embodiments. The forward RF directional coupler 60 is configured to sample forward (pass through) power going from the RF source to the accelerator 12, and the sampled power signal may be used for monitoring purpose. In some cases, the couplers 50, 60 may be implemented using a bi-directional coupler.

In some embodiments, the system 10 may optionally further include an automatic frequency control (AFC) 100. During normal operation (particle acceleration), such automatic frequency control 100 adjusts center frequency of RF power from the RF source 16 to match the resonance frequency of accelerator cavities 12, which may slowly drift as it heats up. The automatic frequency control 100 includes a reflected RF directional coupler 102 for sampling power reflected back from the accelerator 12, and a forward RF directional coupler 104 for sampling forward power towards the accelerator 12, and a processor (which may be the processor 54, or another processor) for performing an analysis using the sampled forward power and reflected power. In some cases, the couplers 102, 104 may be implemented using a bi-directional coupler. Signal reflected from the accelerator 12 contains information that may be used to determine the accelerator 12's frequency matching status. The automatic frequency control 100 may use such information to provide a frequency-locking action for the power source 16. For example, in some embodiments, the automatic frequency control 100 includes a microwave circuit that receives a reflected RF signal and a forward RF signal sensed by the directional couplers 102, 104, respectively, and provides an output that represents a relative phase between the reflected signal and the forward signal. Based on the output, the frequency control 100 may adjust a frequency of the power source 16 so that it is the same as, or closer to, the resonance frequency of the accelerator 12. Thus, the automatic frequency control 100 is desirable because it ensures that RF power is generated at a center frequency that matches accelerator resonance frequency, therefore minimizing reflected power and maximizing available RF power for particle acceleration. Without automatic frequency control, the frequency of the power generator 16 may not be able to follow the slowly drifting resonance frequency that is optimal for accelerator's 12 performance. In some embodiments, the automatic frequency control 100 may be considered to be a part of the frequency tuner 40.

Automatic frequency control has been described in U.S. Pat. No. 3,820,035, the entire disclosure of which is expressly incorporated by reference herein. In other embodiments, instead of being separate from the power modulator system 18, the automatic frequency control 100 may be a part of the power modulator system 18.

As shown in the figure, the accelerator system 10 may also optionally include a manual frequency control 110 for allowing a user to manually adjust a center frequency of the power spectrum. In some embodiments, the control 110 may be a knob at the frequency tuner 40. In other embodiments, the control 110 may be combined with the step control 30 or be combined with the automatic frequency control 100. Also, in other embodiments, the control 110 may be a user interface at a computer, such as the keyboard 112 shown in the figure.

It should be noted that FIG. 1 illustrates schematic diagrams of different embodiments of the system 10, and therefore, the actual implementation of the system 10 does not necessarily require the components to be located relatively to each other as that shown in the figures. Thus, in different embodiments of the system 10, the components can be located relative to each other in manners that are different from that shown in FIG. 1.

Figure 4:
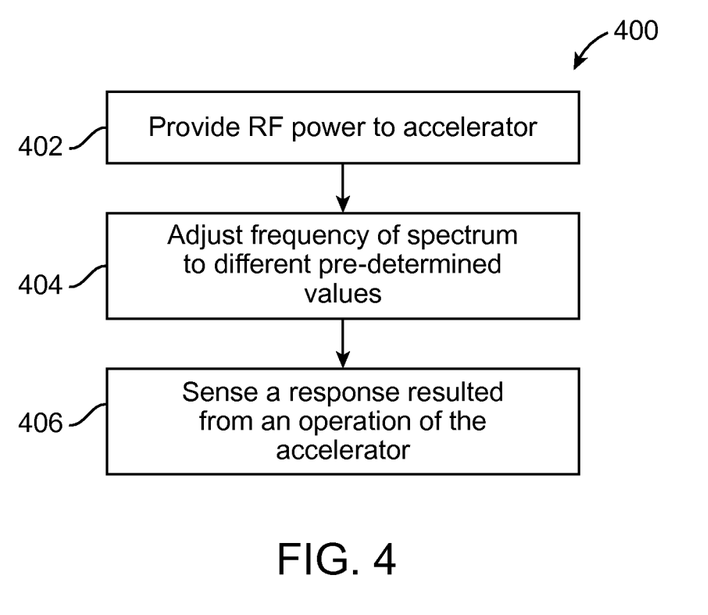
FIG. 4 illustrates a diagnosis method in accordance with some embodiments.

FIG. 4 illustrates a method 400 of diagnosing the accelerator system 10 in accordance with some embodiments. First, RF power is provided to the accelerator 12 (Item 402). In some embodiments, RF power (e.g., a pulsed RF power, a modulated RF power, or continuous wave) is provided from the RF power source 16 to energize the accelerator 12. In the illustrated embodiments, the RF power may be a 2.8-10 GHz, 1-5 us pulse, with 10-1000-Hz pulse repetition frequency, and a peak power of 1-10 MW. In other embodiments, the RF power can have other characteristics—i.e., with ranges that are different from those described.

The center frequency of the spectrum associated with the power provided by the power source 16 is adjusted to different pre-determined values (Item 404). In some embodiments, the adjustment of the center frequency through the frequency range defined by the pre-determined values may be performed within a short period (e.g., within a few seconds, such as within 5 seconds, or less). In such situation, resonance frequency of accelerator cavities may be considered as not changing for the duration. In other embodiments, the adjustment of the center frequency may be performed within a duration that is longer than 5 seconds. In some embodiments, the RF power source may not be producing RF power when no measurement is going on, so that resonance frequency of accelerator cavities will not significantly drift due to heating. In some embodiments, the adjustment of the center frequency may be performed automatically using a control. The control may be the frequency tuner 40, the step control 30, the processor 54, or combination thereof. In other embodiments, the adjustment of the center frequency may be performed manually (e.g., using the control 110).

Next, a response resulted from an operation of the accelerator 12 is then recorded (Item 406). In the illustrated embodiments, the directional coupler 50 samples the reflected RF power from the accelerator 12. The sensor 52 receives the RF signal (sampled from reflected power) from the directional coupler 50 and generates a voltage signal in response to the reflected power that corresponds with the center frequency of the forward power spectrum. When RF power is generated at each center frequency point, the processor 54 records the reflected RF signal from sensor 52. The resulting data pairs (center frequency vs. reflected RF power) form a spectrum (which may be recorded), and the spectrum may be used to determine whether the RF source 16 is working properly. Thus, the spectrum response is based at least in part on the adjusted frequency of the RF power through the frequency range. The resulting spectrum may be considered as a convolution of the RF source spectrum 200 and the filter response 201.

The resulting spectrum may be displayed in a screen for view by a user. In some embodiments, the resulting spectrum may be stored in a non-transitory medium for later use. For example, in some embodiments, the resulting spectrum, which is generated when the accelerator system 10 is working properly, may be used as a reference spectrum for comparison with later generated spectrums. For example, in some embodiments, the stored spectrum may be compared as a reference spectrum with another spectrum generated from a later diagnostic procedure, and the comparison result may be used to determine whether the accelerator system 10 is performing properly. For example, if the later spectrum generated from the current or recent diagnostic procedure looks like the stored spectrum (generated when the accelerator system 10 is working properly), then it may be determined that the accelerator system 10 (e.g., the power source 16) is still working properly. On the other hand, if the later spectrum looks different from the stored spectrum, it may then be determined that the accelerator system 10 (e.g., the power source 16) is not working properly.

In other embodiments, if a reference spectrum was already created and stored previously, the resulting spectrum from Item 404 may be used to compare with the stored reference spectrum to determine if the accelerator is working properly.

In one or more embodiments, the comparing of the reference spectrum with a later obtained spectrum may be performed manually, or automatically using a processor. For example, in some embodiments, a processor (e.g., the processor 54) may be configured to perform curve analysis, image analysis, or any of other types of analysis to determine whether the later obtained spectrum is different enough from the reference spectrum that is indicative of the accelerator system 10 not working properly. In some embodiments, the processor may be configured to measure the width of main lobe of the recorded spectrum. If the width of the main lobe stays as narrow as in the reference spectrum, then it may be determined that the RF source 16 is working properly. On the other hand, if the main lobe width is wider than that of the stored spectrum by a predetermined percentage, then it may be determined that the RF source 16 is not working properly.

As illustrated in the above embodiments, the method 400 and system 10 are advantageous in that they can detect the situation in which the power source 16 produces RF power at normal power level, but its spectrum becomes bad. This may occur when the power source 16 malfunctions in a way that it still produces RF power output, but the spectral quality of the power deteriorates. Such problems may not be detectable using existing RF power monitors (directional couplers and RF detectors or sensors). Also, because the method 400 and system 10 use on-board components to perform the diagnosis, they obviate the need to use a sophisticated spectrum analyzer for off-line diagnosis, which is expensive, difficult, and cumbersome to use. The on-board components described herein are simple and inexpensive to implement and use, and once implemented at the system 10, they'll always be available to perform diagnostic procedures. Thus, in some cases, the embodiments of the accelerator system 10 described herein allow a diagnostic procedure to be performed every time before the accelerator system 10 is used. Also, the method 400 and system 10 obviates the need to adjust any filter frequency of a band pass filter that may be included in spectrum analyzers, which may be configured to pass signal (e.g., sampled RF signal) through a narrow band pass filter and record the through power.

Figure 6:
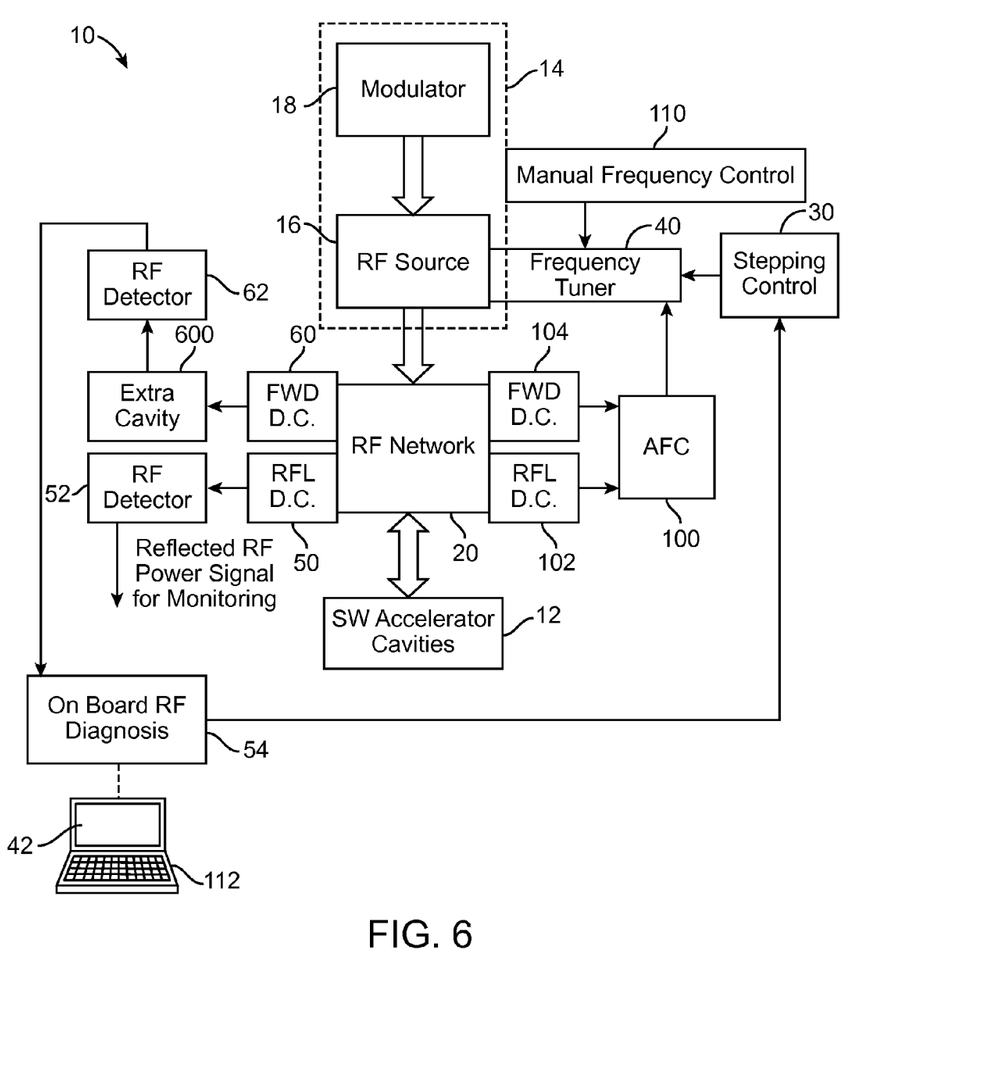
FIG. 6 illustrates a block diagram of another accelerator system in accordance with other embodiments.

It should be noted that the accelerator system 10 is not limited to the examples described, and that the accelerator system 10 may have other configurations in other embodiments. For example, in other embodiments, instead of using the reflected power signals transmitted back from the accelerator 12 for diagnosis of the accelerator system 10, forward (pass-through) power signals may be used. FIG. 6 illustrated an accelerator system 10 that uses forward power signals for diagnosis purpose in accordance with some embodiments. The accelerator system 10 is the same as that shown in FIG. 1, except that the sensor 52 is not coupled to the processor 54 for RF spectrum diagnosis. Instead, the processor 54 is configured to receive signals from the sensor 62 that is coupled indirectly to the directional coupler 60 through an extra RF cavity 600. The cavity 600 may be the same or similar to one of the accelerator cavities in some embodiments. The portion of RF signal spectrum from forward RF directional coupler 60 that overlaps with resonance frequency of cavity 600 will pass through to sensor 62. When the RF source center frequency matches the resonance frequency of cavity 600, output voltage on sensor 62 is maximized. When the RF source frequency is completely off from the resonance frequency of cavity 600, net output voltage at sensor 62 is zero. An advantage of using the extra cavity 600 is that the sampled RF signal from forward RF directional coupler 60 is at low power level. Thus, the cavity will not be heated up, and the extra cavity 600 will not have resonance frequency drift even after long period of diagnostic measurement.

Figure 7A:
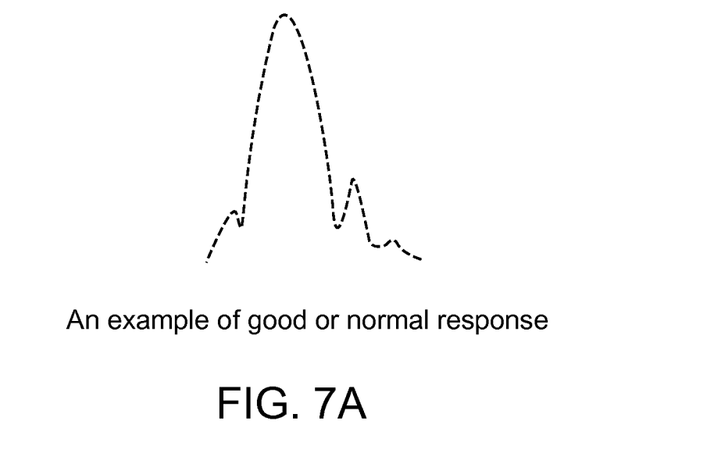
FIGS. 7A-7B illustrate examples of response spectrums in accordance with some embodiments.

During RF spectrum diagnosis, the frequency tuner 40, controlled by processor 54 and steeping control 30, operates the RF power source 16 to generate power across a frequency range, thereby placing the center frequency of the power spectrum at different values, one data point at a time. At the same time, the forward RF power towards the accelerator 12 is sampled by the directional coupler 60 and is transmitted to the sensor 62 through the cavity 600. The sensor 62 generates signals in response to the RF signal that passes through cavity 600 while the center frequency of the forward RF power spectrum is adjusted to different pre-determined values, and transmits the signals to the processor 54 for processing. When RF power is generated at each center frequency point, the processor 54 records the reflected RF signal from sensor 52. The resulting data pairs (e.g., center frequency vs. reflected RF power) form a spectrum (which may be recorded), and the spectrum may be used to determine whether the RF source 16 is working properly. In some embodiments, the signals from the sensor 62 may be displayed in a screen 42 in a form of a spectrum. FIG. 7A illustrates an example of a spectrum 700 generated using the sensor 62. The resulting spectrum may be considered as a convolution of the RF source spectrum 200 and the filter response 201

Figure 7B:
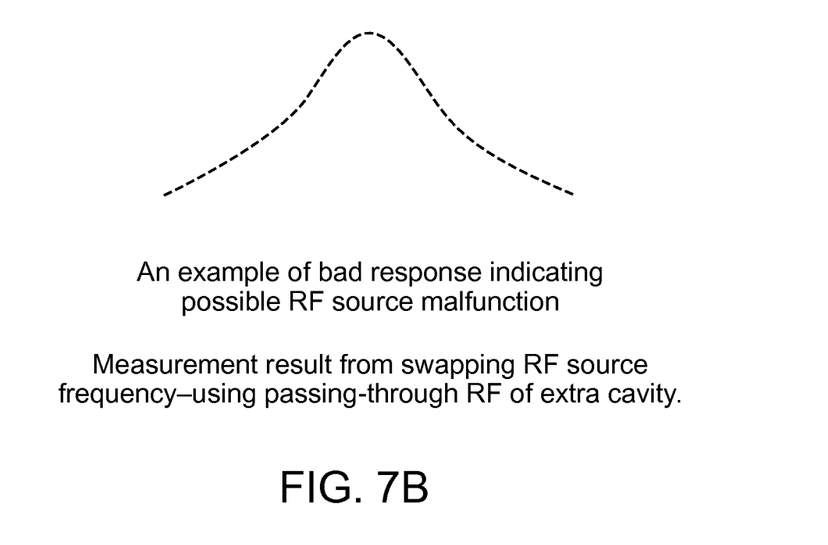

Also, in some embodiments, the spectrum 700 may be stored in a non-transitory medium for further processing. Such spectrum 700, which is generated when the accelerator system 10 is working properly, may be used as a reference spectrum for comparison with later generated spectrums. For example, in some embodiments, the stored spectrum 700 resulted from a previous diagnostic procedure may be compared as a reference spectrum with another spectrum generated from a current or more recent diagnostic procedure, and the comparison result may be used to determine whether the accelerator system 10 is performing properly. For example, if the new spectrum generated from the current or recent diagnostic procedure looks like the stored spectrum (generated when the accelerator system 10 is working properly), then it may be determined that the accelerator system 10 (e.g., the RF power source 16) is still working properly. On the other hand, if the new spectrum (like that shown in FIG. 7B) looks different from the stored spectrum, it may then be determined that the accelerator system 10 (e.g., the RF power source 16) is not working properly. In some embodiments, the processor 54 may be a comparator configured (e.g., built and/or programmed) to compare the output from the sensor 62 with a previously stored response. The comparator 54 may be implemented using a processor, a computer, or any other circuit.

The system of FIG. 6 may be useful for diagnosing the RF power source 16, or a part of a RF network (e.g., a circulator at the RF network 20) depending on the location at which the cavity filter measurement is taken.

Figure 8:
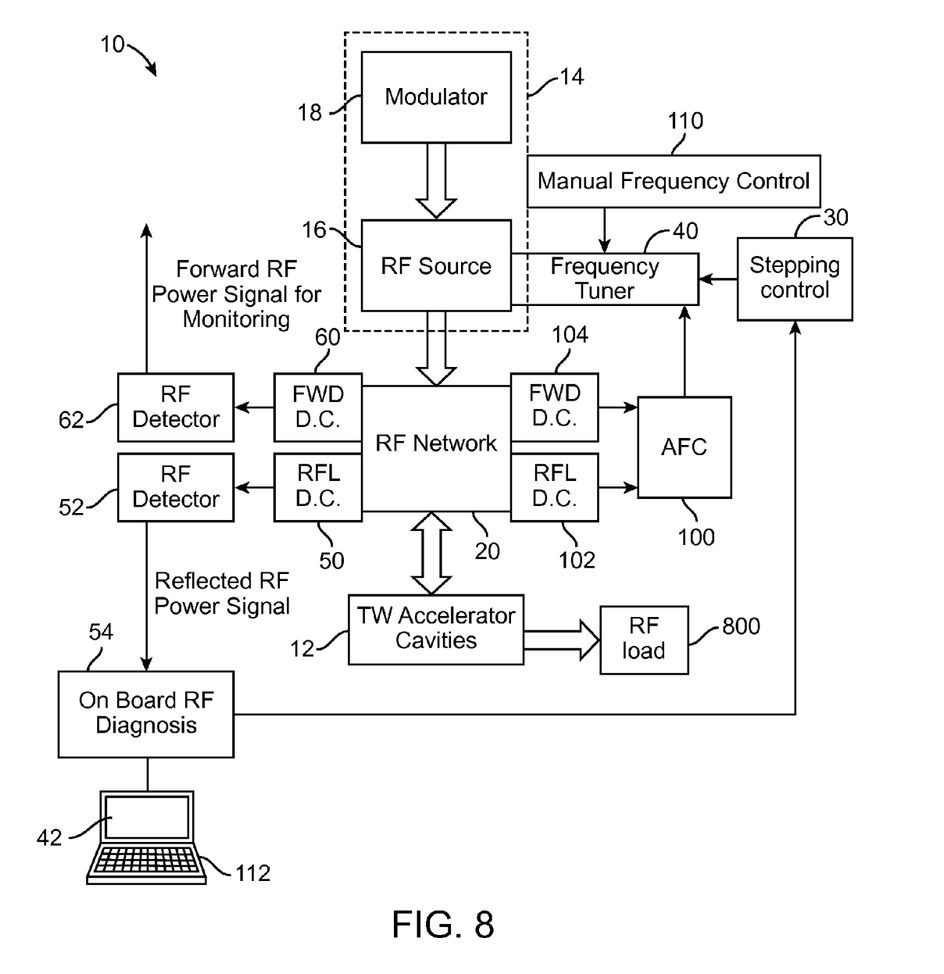
FIG. 8 illustrates a block diagram of another accelerator system in accordance with other embodiments.

In the above embodiments, the accelerator 12 may be a standing wave particle accelerator. In other embodiments, the accelerator 12 may be a traveling wave accelerator. FIG. 8 illustrates an accelerator system 10 in accordance with some embodiments. The system 10 is the same as that described with reference to FIG. 1, except that the accelerator 12 is a traveling wave particle accelerator 12. The traveling wave particle accelerator 12 is coupled to a RF load 800. The diagnostic technique described may be similarly applied for the system 10 of FIG. 8. In particular, during RF diagnosis, the frequency tuner 40, controlled by processor 54 and stepping control 30, operates the power source 16 to generate power across a frequency range, thereby placing the center frequency of the power spectrum at different values. At the same time, the reflected power from the traveling wave accelerator 12 is coupled by the reflected RF directional coupler 50 and is transmitted to the sensor 52. The sensor 52 generates signals in response to the reflected power while the center frequency of the forward power spectrum is adjusted to different pre-determined values, one data point at a time, and transmits the signals to the processor 54 for processing, one data point at a time. The resulting data pairs (center frequency vs. reflected RF power) form a spectrum (which may be recorded), and the spectrum may be used to determine whether the RF source 16 is working properly. In some embodiments, the signals from the sensor 52 may be displayed in a screen 42 in a form of a spectrum (like that shown in FIG. 3). Also, in some embodiments, the spectrum may be stored in a non-transitory medium for further processing. Such spectrum, which is generated when the traveling wave accelerator system 10 is working properly, may be used as a reference spectrum for comparison with later generated spectrums. For example, in some embodiments, the stored spectrum resulted from a previous diagnostic procedure may be compared as a reference spectrum with another spectrum generated from a current or more recent diagnostic procedure, and the comparison result may be used to determine whether the accelerator system 10 is performing properly. For example, if the new spectrum (like that shown in FIG. 5A) generated from the current or recent diagnostic procedure looks like the stored spectrum (generated when the accelerator system 10 is working properly) like that shown in FIG. 3, then it may be determined that the traveling wave accelerator system 10 (e.g., the RF power source 16) is still working properly. On the other hand, if the new spectrum (like that shown in FIG. 5B) looks different from the stored spectrum, it may then be determined that the traveling wave accelerator system 10 (e.g., the RF power source 16) is not working properly. In some embodiments, the processor 54 may be a comparator configured (e.g., built and/or programmed) to compare the output from the sensor 52 with a previously stored response.

Figure 9:
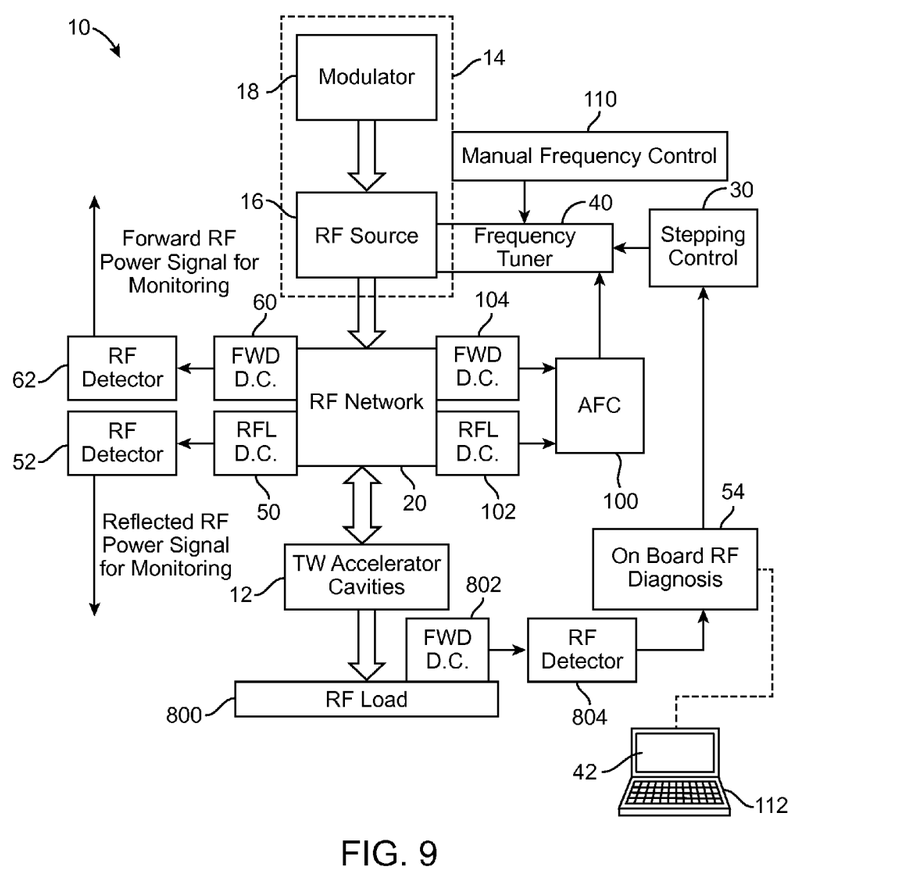
FIG. 9 illustrates a block diagram of another accelerator system in accordance with other embodiments.

Also, in other embodiments in which the accelerator 12 is a traveling wave accelerator, the system 10 may use the forward RF power that transmit through the traveling wave accelerator to diagnose the system 10. FIG. 9 illustrates an accelerator system 10 in accordance with some embodiments. The system 10 is the same as that described with reference to FIG. 8, except that the processor 54 is not coupled to the sensor 52 for receiving signals for reflected power. Instead, the system 10 includes a directional coupler 802 coupled to the RF load 800, and a sensor 804 coupled to the directional coupler 802. The processor 54 is coupled to the sensor 804 for receiving signals from the sensor 804 that indicate corresponding forward power signals received at the coupler 802.

The diagnostic technique described may be similarly applied for the system 10 of FIG. 9. In particular, during RF diagnosis, the frequency tuner 40, controlled by processor 54 and stepping control 30, operates the power source 16 to generate power across a frequency range, thereby placing the center frequency of the power spectrum at different values, one data point at a time. At the same time, the forward power through the traveling wave accelerator 12 is coupled by the directional coupler 802 and is transmitted to the sensor 804. The sensor 804 generates signals in response to the forward RF power while the center frequency of the forward power spectrum is adjusted to different pre-determined values, and transmits the signals to the processor 54 for processing, one data point at a time. The resulting data pairs (center frequency vs. reflected RF power) form a spectrum (which may be recorded), and the spectrum may be used to determine whether the RF source 16 is working properly. In some embodiments, the signals from the sensor 52 may be displayed in a screen 42 in a form of a spectrum (like that shown in FIG. 7A). Also, in some embodiments, the spectrum may be stored in a non-transitory medium for further processing. Such spectrum, which is generated when the traveling wave accelerator system 10 is working properly, may be used as a reference spectrum for comparison with later generated spectrums. For example, in some embodiments, the stored spectrum resulted from a previous diagnostic procedure may be compared as a reference spectrum with another spectrum generated from a current or more recent diagnostic procedure, and the comparison result may be used to determine whether the accelerator system 10 is performing properly. For example, if the new spectrum generated from the current or recent diagnostic procedure looks like the stored spectrum (generated when the accelerator system 10 is working properly), then it may be determined that the traveling wave accelerator system 10 (e.g., the RF power source 16) is still working properly. On the other hand, if the new spectrum (like that shown in FIG. 7B) looks different from the stored spectrum, it may then be determined that the traveling wave accelerator system 10 (e.g., the RF power source 16) is not working properly. In some embodiments, the processor 54 may be a comparator configured (e.g., built and/or programmed) to compare the output from the sensor 52 with a previously stored response.

It should be noted that the accelerator 12 described in the above examples is not limited to an electron accelerator, and may be other types of accelerator for accelerating other particles (e.g., protons, neutrons, etc.).

In one or more embodiments, the processor 54 may be implemented using a programmable logic controller (PLC), which includes a CPU.

Computer System Architecture

Figure 10:
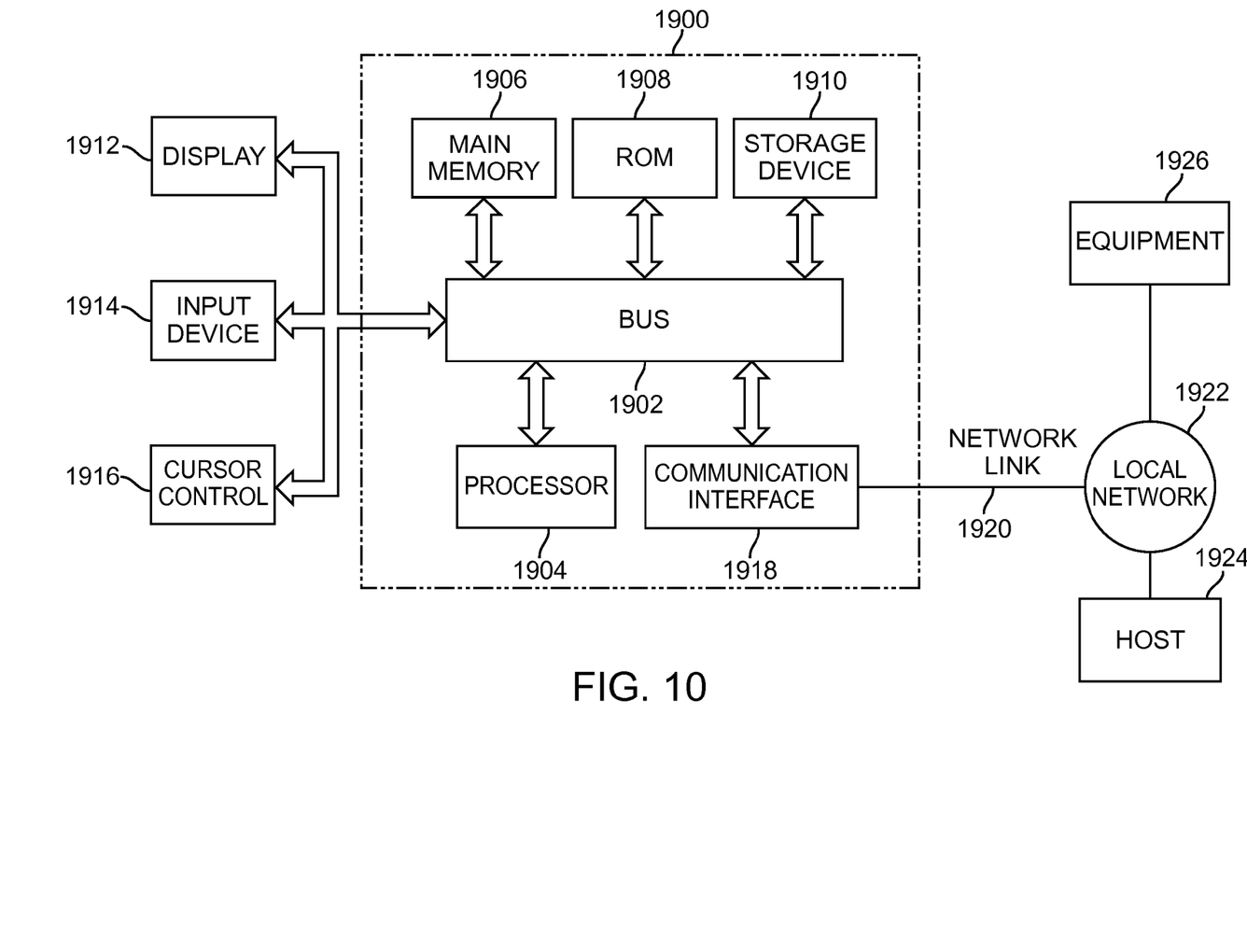
FIG. 10 illustrates a computer system that may be used to implement embodiments described herein in accordance with some embodiments.

FIG. 10 is a block diagram that illustrates an embodiment of a computer system 1900 upon which embodiments described herein may be implemented. Computer system 1900 includes a bus 1902 or other communication mechanism for communicating information, and a processor 1904 coupled with the bus 1902 for processing information. The processor 1904 may be an example of the processor 54 of FIG. 1, or another processor that is used to perform various functions described herein. Also, in some embodiments, the computer system 1900 may be used to implement the components 54, 42, 112 in the accelerator system 10. In other embodiments, the computer system 1900 may be used to implement the components 30, 54, 42, 112 in the accelerator system 10. The computer system 1900 also includes a main memory 1906, such as a random access memory (RAM) or other dynamic storage device, coupled to the bus 1902 for storing information and instructions to be executed by the processor 1904. The main memory 1906 also may be used for storing temporary variables or other intermediate information during execution of instructions to be executed by the processor 1904. The computer system 1900 further includes a read only memory (ROM) 1908 or other static storage device coupled to the bus 1902 for storing static information and instructions for the processor 1904. A data storage device 1910, such as a magnetic disk or optical disk, is provided and coupled to the bus 1902 for storing information and instructions.

The computer system 1900 may be coupled via the bus 1902 to a display 1912, such as a cathode ray tube (CRT), for displaying information to a user. An input device 1914, including alphanumeric and other keys, is coupled to the bus 1902 for communicating information and command selections to processor 1904. Another type of user input device is cursor control 1916, such as a mouse, a trackball, or cursor direction keys for communicating direction information and command selections to processor 1904 and for controlling cursor movement on display 1912. This input device typically has two degrees of freedom in two axes, a first axis (e.g., x) and a second axis (e.g., y), that allows the device to specify positions in a plane.

The computer system 1900 may be used for performing various functions (e.g., calculation) in accordance with the embodiments described herein. According to one embodiment, such use is provided by computer system 1900 in response to processor 1904 executing one or more sequences of one or more instructions contained in the main memory 1906. Such instructions may be read into the main memory 1906 from another computer-readable medium, such as storage device 1910. Execution of the sequences of instructions contained in the main memory 1906 causes the processor 1904 to perform the process steps described herein. One or more processors in a multi-processing arrangement may also be employed to execute the sequences of instructions contained in the main memory 1906. In alternative embodiments, hard-wired circuitry may be used in place of or in combination with software instructions to implement one or more features of the embodiments described herein. Thus, embodiments described herein are not limited to any specific combination of hardware circuitry and software.

The term "computer-readable medium" as used herein refers to any medium that participates in providing instructions to the processor 1904 for execution. Such a medium may take many forms, including but not limited to, non-volatile media, volatile media, and transmission media. Non-volatile media includes, for example, optical or magnetic disks, such as the storage device 1910. A non-volatile medium may be considered to be an example of a non-transitory medium. Volatile media includes dynamic memory, such as the main memory 1906. A volatile medium may be considered to be another example of a non-transitory medium. Transmission media includes coaxial cables, copper wire and fiber optics, including the wires that comprise the bus 1902. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1904 for execution. For example, the instructions may initially be carried on a magnetic disk of a remote computer. The remote computer can load the instructions into its dynamic memory and send the instructions over a telephone line using a modem. A modem local to the computer system 1900 can receive the data on the telephone line and use an infrared transmitter to convert the data to an infrared signal. An infrared detector coupled to the bus 1902 can receive the data carried in the infrared signal and place the data on the bus 1902. The bus 1902 carries the data to the main memory 1906, from which the processor 1904 retrieves and executes the instructions. The instructions received by the main memory 1906 may optionally be stored on the storage device 1910 either before or after execution by the processor 1904.

The computer system 1900 also includes a communication interface 1918 coupled to the bus 1902. The communication interface 1918 provides a two-way data communication coupling to a network link 1920 that is connected to a local network 1922. For example, the communication interface 1918 may be an integrated services digital network (ISDN) card or a modem to provide a data communication connection to a corresponding type of telephone line. As another example, the communication interface 1918 may be a local area network (LAN) card to provide a data communication connection to a compatible LAN. Wireless links may also be implemented. In any such implementation, the communication interface 1918 sends and receives electrical, electromagnetic or optical signals that carry data streams representing various types of information.

The network link 1920 typically provides data communication through one or more networks to other devices. For example, the network link 1920 may provide a connection through local network 1922 to a host computer 1924 or to equipment 1926 such as a radiation beam source or a switch operatively coupled to a radiation beam source. The data streams transported over the network link 1920 can comprise electrical, electromagnetic or optical signals. The signals through the various networks and the signals on the network link 1920 and through the communication interface 1918, which carry data to and from the computer system 1900, are exemplary forms of carrier waves transporting the information. The computer system 1900 can send messages and receive data, including program code, through the network (s), the network link 1920, and the communication interface 1918.

Although particular embodiments have been shown and described, it will be understood that they are not intended to limit the claimed inventions, and it will be obvious to those skilled in the art that various changes and modifications may be made. The specification and drawings are, accordingly, to be regarded in an illustrative rather than restrictive sense. The claimed inventions are intended to cover alternatives, modifications, and equivalents.

What is claimed:

1. An RF accelerator system, comprising:
   an accelerator;
   an RF source coupled to the accelerator for providing RF power to the accelerator;
   a control for adjusting a frequency of the RF power provided by the RF source through a frequency range; and
   a sensor for sensing a response resulted from an operation of the accelerator based at least in part on the adjusted frequency of the RF power through the frequency range.

2. The accelerator system of claim 1, wherein the control is configured to adjust the frequency of the RF power by serially stepping the frequency to a plurality of pre-determined values.

3. The accelerator system of claim 1, wherein the frequency comprises a center frequency, the RF power comprises a spectrum with the center frequency, and the control is configured for adjusting the center frequency of the spectrum of the RF power.

4. The accelerator system of claim 1, wherein the response is also based on a reflected RF power from the accelerator.

5. The accelerator system of claim 4, wherein the adjusted frequency of the RF power produces an RF source spectrum, and the sensor is configured to sense a convolution of the RF source spectrum and the reflected RF power as the response.

6. The accelerator system of claim 1, wherein the response is also based on a forward RF power passing through a RF cavity that is coupled to accelerating cavities of the accelerator.

7. The accelerator system of claim 6, wherein the adjusted frequency of the RF power produces an RF source spectrum, and the sensor is configured to sense a convolution of the RF source spectrum and the forward RF power passing through the RF cavity as the response.

8. The accelerator system of claim 1, wherein the frequency range comprises a predetermined range, and the control is configured for adjusting the frequency of the RF power through the predetermined range within a few seconds.

9. The accelerator system of claim 1, further comprises a comparator for comparing the measured response to a previously recorded response.

10. The accelerator system of claim 1, wherein the sensor is an on-board sensor.

11. The accelerator system of claim 1, wherein the accelerator comprises a standing wave accelerator.

12. The accelerator system of claim 1, wherein the accelerator comprises a traveling wave accelerator.

13. The accelerator system of claim 1, wherein the accelerator is a part of a treatment system.

14. The accelerator system of claim 1, wherein the accelerator is a part of an imaging system.

15. The accelerator system of claim 1, wherein the accelerator is a part of an inspection system.

16. A method of diagnosing a RF spectrum in an accelerator system, comprising:
    providing RF power to an accelerator;
    adjusting a frequency of the RF power through a frequency range; and
    sensing a response resulted from an operation of the accelerator, the response being based at least in part on the adjusted frequency of the RF power through the frequency range.

17. The method of claim 16, wherein the act of adjusting the frequency of the RF power comprises serially stepping the frequency to a plurality of pre-determined values.

18. The method of claim 16, wherein the frequency comprises a center frequency, the RF power comprises a spectrum with the center frequency, and the act of adjusting comprises adjusting the center frequency of the spectrum of the RF power.

19. The method of claim 16, wherein the response is also based on a reflected RF power from the accelerator.

20. The method of claim 19, wherein the adjusted frequency of the RF power produces a RF source spectrum, and the act of sensing comprises sensing a convolution of the RF source spectrum and the reflected RF power as the response.

21. The method of claim 16, wherein the response is also based on a forward RF power passing through a RF cavity that is coupled to accelerating cavities of the accelerator.

22. The method of claim 21, wherein the adjusted frequency of the RF power produces a RF source spectrum, and the act of sensing comprises sensing a convolution of the RF source spectrum and the forward RF power passing through the RF cavity as the response.

23. The method of claim 16, wherein the frequency range comprises a predetermined range, and the frequency of the RF power is adjusted through the predetermined range within a few seconds.

24. The method of claim 16, further comprises comparing the measured response to a previously recorded response.

25. The method of claim 16, wherein the act of sensing is performed using an on-board sensor.

26. The method of claim 16, wherein the accelerator comprises a standing wave accelerator.

27. The method of claim 16, wherein the accelerator comprises a traveling wave accelerator.

28. The method of claim 16, wherein the accelerator is a part of a treatment system.

29. The method of claim 16, wherein the accelerator is a part of an imaging system.

30. The method of claim 16, wherein the accelerator is a part of an inspection system.

* * * * *